US012754269B2

(12) United States Patent
Liu et al.

(10) Patent No.: US 12,754,269 B2
(45) Date of Patent: Oct. 6, 2026

(54) REDUCING PERIPHERAL NERVE STIMULATION IN A SUBJECT DURING A MAGNETIC RESONANCE IMAGING SCAN

(71) Applicant: Siemens Healthineers AG, Forchheim (DE)

(72) Inventors: Wei Liu, Erlangen (DE); David Grodzki, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 123 days.

(21) Appl. No.: 18/651,812

(22) Filed: May 1, 2024

(65) Prior Publication Data

US 2024/0393416 A1 Nov. 28, 2024

(30) Foreign Application Priority Data

May 24, 2023 (EP) .................................... 23175024

(51) Int. Cl.

*G01R 33/54* (2006.01)
*A61B 5/00* (2006.01)
*G01R 33/28* (2006.01)
*G01R 33/561* (2006.01)

(52) U.S. Cl.

CPC .......... *G01R 33/543* (2013.01); *A61B 5/0044* (2013.01); *G01R 33/288* (2013.01); *G01R 33/561* (2013.01)

(58) Field of Classification Search

CPC .. G01R 33/543; G01R 33/561; G01R 33/288; A61B 5/0044

See application file for complete search history.

(56) References Cited

U.S. PATENT DOCUMENTS

2017/0205483 A1 7/2017 Feiweier et al.
2021/0011100 A1* 1/2021 Gong .................... G01R 33/38

FOREIGN PATENT DOCUMENTS

EP 4009066 A1 6/2022

OTHER PUBLICATIONS

Davids, Mathias, et al. "Optimization of MRI gradient coils with explicit peripheral nerve stimulation constraints." IEEE transactions on medical imaging 40.1 (2020): 129-142.

(Continued)

*Primary Examiner* — Rishi R Patel
(74) *Attorney, Agent, or Firm* — Lempia Summerfield Katz LLC

(57) ABSTRACT

Peripheral nerve stimulation (PNS) in a subject is reduced during a magnetic resonance imaging scan of the subject using a magnetic resonance system (1) having three physical gradient axes. The magnetic resonance imaging scan is planned by selecting an imaging protocol and positioning a field-of-view of the scan obliquely through the subject. An estimate of the PNS for the planned magnetic resonance imaging scan is determined. A gradient polarity of at least one logical gradient axis of the scan that is not parallel to any of the physical gradient axes is inverted, and an estimate of the PNS for the magnetic resonance imaging scan with the inverted polarity is determined. The gradient polarity which has the lowest PNS is selected. The magnetic resonance imaging scan is performed on the subject with the selected gradient polarity.

19 Claims, 5 Drawing Sheets

(56) References Cited

OTHER PUBLICATIONS

Ham, C. L. G., et al. "Peripheral nerve stimulation during MRI: effects of high gradient amplitudes and switching rates." Journal of Magnetic Resonance Imaging 7.5 (1997): 933-937.
Hebrank, Franz X., and Matthias Gebhardt. "Safe-model-a new method for predicting peripheral nerve stimulations in MRI." Proc Intl Soc Mag Res Med. vol. 8. 2000.
In, Myung-Ho, et al. "Reducing PNS with minimal performance penalties via simple pulse sequence modifications on a high-performance compact 3T scanner." Physics in Medicine & Biology 65.15 (2020): 15NT02. pp. 1-14.

* cited by examiner

REDUCING PERIPHERAL NERVE STIMULATION IN A SUBJECT DURING A MAGNETIC RESONANCE IMAGING SCAN

RELATED APPLICATION

This application claims the benefit of EP 23175024.1, filed on May 24, 2023, which is hereby incorporated by reference in its entirety.

FIELD

The present disclosure relates to a method for reducing peripheral nerve stimulation in a subject during a magnetic resonance imaging scan and a corresponding computer program and magnetic resonance imaging system.

Independent of the grammatical term usage, individuals with male, female or other gender identities are included within the term.

BACKGROUND

In magnetic resonance (MR) imaging (MRI), high-performance gradients of the most recent MR scanner generations can improve the image quality and the speed of the imaging process. High-performance gradients are gradients that can reach particularly high maximum gradient amplitudes and maximum slew rates. For example, the MAGNETOM PRISMA MR system by Siemens Healthcare has a maximum gradient of 80 mT/m and maximum slew rates of 200 T/m/s. These high-performance gradients can be beneficial for many applications. For example, in diffusion-weighted MRI, a high gradient amplitude can reduce the diffusion encoding time and improve a signal-to-noise ratio by reducing the T2 decay. A high gradient slew rate can, for example, enable a shorter echo spacing and lead to reduced distortion.

However, the application of high gradient amplitudes and fast switching rates comes together with short rise times for the gradient field and with high changes of the magnetic flux density in a patient that is examined via MRI. This may cause peripheral nerve stimulation (PNS) in the patients, as is explained by C. L. G. Ham et al. in “A. Peripheral Nerve Stimulation during MRI: Effects of High Gradient Amplitudes and Switching Rates”, J. Magn. Reson. 1997; 7:933-937. PNS may cause discomfort in the patient and, hence, sets a physiologic limit for MRI applications.

A relatively straight-forward way to respond to this problem is to add conservative constraints limiting the gradient amplitude and slew rate across a pulse sequence. However, this approach naturally limits the achievable gradient performance and may lead to suboptimal imaging performance.

An alternative approach is described by Myung-Ho In et al. in “Reducing PNS with Minimal Performance Penalties via Simple Pulse Sequence Modifications on a High-Performance Compact 3T Scanner”, Phys Med Biol. 2020; 65 (15). Hence, specific gradient lobes may be derated to minimize PNS more efficiently than by changing all gradients. However, this approach is sequence-specific and cannot be generalized. Knowledge of the gradient lobes that mainly contribute to PNS is required to apply this approach.

Another alternative approach is proposed by M. Davids et al. in “Optimization of MRI gradient coils with explicit peripheral nerve stimulation constraints”, IEEE Trans Med Imaging. 2020; 40:129-142. Hence, PNS effects may be incorporated into the coil winding optimization process such that the PSN is minimized. However, this comes at the cost of penalties in coil inductance and gradient linearity.

SUMMARY AND DETAILED DESCRIPTION

It is therefore an object to provide reduction of peripheral nerve stimulation in a subject during a magnetic resonance imaging scan while having only little or, preferably, no negative impact on scan quality.

This object is met or exceeded by a method, a computer program stored on a non-transitory computer readable medium, and a magnetic resonance imaging system. Further advantages and features result from the dependent claims, the description and the attached figures.

According to a first aspect, a method for reducing peripheral nerve stimulation in a subject during a magnetic resonance imaging scan of the subject using a magnetic resonance system having three physical gradient axes is provided. The method includes the following acts:

(a) planning the magnetic resonance imaging scan by selecting an imaging protocol and positioning a field-of-view of the scan obliquely through the subject, such that at least two of the logical gradient axes of the scan are not parallel to any of the physical gradient axes;

(b) determining an estimate of the overall peripheral nerve stimulation for the planned magnetic resonance imaging scan;

(c) inverting the gradient polarity of at least one logical gradient axis of the scan that is not parallel to any of the physical gradient axes and determining an estimate of the overall peripheral nerve stimulation for the planned magnetic resonance imaging scan with the inverted polarity;

(d) selecting the gradient polarity of the at least one logical gradient axis which has the lowest overall peripheral nerve stimulation, in particular the lowest maximum of the overall peripheral nerve stimulation across the imaging protocol; and (e) performing the planned magnetic resonance imaging scan on the subject with the selected gradient polarity.

The subject may in particular be a patient and/or a human being or animal.

Magnetic resonance imaging (MRI) systems typically have three physical gradient axes defined by the arrangement of three gradient coils. The physical gradient axes are typically defined as the directions in which the magnetic fields generated by the three gradient coils have their gradient, i.e., in which the magnetic fields vary at least approximately linearly. The physical gradient axes are often oriented along the main axes of the MRI system, i.e., along the x-, y-, and z-axes, wherein the z-axis is the direction of the main magnetic field and is typically oriented along the axis of the bore. It has been found that the contribution of these physical gradient axes to the peripheral nerve stimulation (PNS) may differ significantly from one another, because the gradient fields are generated by different gradient coils. This may be due to the fact that the nerve stimulation is caused by the varying electric fields, which however may not be the same for each gradient coil, even if the magnetic field is comparable. Hence, one physical gradient axis (corresponding to a gradient coil) may induce a much stronger PNS at the same magnetic field strength and switching rate than another one. Furthermore, the direction of the magnetic fields relative to the subject can also be relevant in some cases. Since the subject is usually placed in a same or similar way during a particular protocol or even during various protocols, this effect may typically be reproduceable, potentially leading or contributing to a distinctive difference in PNS caused by different physical gradient axes. The logical gradient axes are typically the slice selection axis ($G_s$), the phase encoding axis ($G_p$) and the signal read-out axis ($G_r$). According to an embodiment, the at least one logical axis includes the read-out axis, the slice-select axis and/or the phase-encode axis or axes. Multiple phase-encode axes may be applied. According to an embodiment, the at least one logical axis includes the slice-select axis; wherein the polarity of the frequency of the RF pulses is selected according to the selected polarity of the slice-select axis. In particular, if the slice axis is inverted, it is usually necessary to also invert the frequency of the RF pulses. When images are taken in standard axial, coronal, or sagittal orientation, the physical gradient axes ($G_x$, $G_y$, $G_z$) are each parallel to one of the logical gradient axes and thus basically identical. This disclosure aims at the case where the coordinate system of the logical axes is rotated with respect to the coordinate system of the gradient axes about at least one axis. For example, a rotation about the z-axis (assuming this corresponds to a rotation around $G_z$ and $G_s$) may lead to the logical gradient axes $G_p$ and $G_r$ each being related to both the $G_x$ and the $G_y$ axis such that (Eq. 1):

$$G_x = G_r\cos\theta - G_p\sin\theta$$

$$G_y = G_r\sin\theta + G_p\cos\theta$$

$$G_z = G_s$$

Herein, two logical gradient axes, namely $G_p$ and $G_r$, are not parallel to any physical gradient axis, if the angle of rotation θ is not zero. In other words, an oblique plane is imaged that is rotated around one of the physical gradient axes. Hence, the PNS caused by a logical gradient axis may thus depend on two different physical gradient axes. This oblique imaging may be advantageous to analyse objects, in particular organs, with a correspondingly oblique orientation. For example, oblique scanning may be useful for imaging of the heart. On the other hand, the PSN effect may be increased due to simultaneously using more than one physical gradient axis. It has been found that the dependency of the logical gradient axes on more than one physical gradient axis may also be used to advantageously optimize, i.e., minimize, the PNS for these oblique scans. Since the PNS caused by individual physical gradient axis can be determined according to state-of-the-art methods, for example as proposed by Franz X. Hebrank and Matthias Gebhardt in "SAFE-Model—A New Method for Predicting Peripheral Nerve Stimulations in MRI", Proceedings of the 8th Annual Meeting of ISMRM; Denver. 2000; 2007, the contribution of the individual physical gradient axes to the PNS may be taken as a basis to determine the overall PNS caused by the at least one logical gradient axis. Generally, the logical gradient axes can each have two polarities, i.e., in positive axis direction or in negative axis direction. Hence, dependant on the polarity of the logical gradient axis, the contribution of the physical gradient axes to each logical gradient axis may vary. By inverting the polarity, it may thus be possible to "shift" gradient activity from one physical gradient axis to another. For example, following the above example, inverting the polarity of the read-out axis (i.e., $G_r$ being replaced by $-G_r$) leads to the following dependencies (Eq.2):

$$G_{x'} = -G_r\cos\theta - G_p\sin\theta$$

$$G_{y'} = -G_r\sin\theta + G_p\cos\theta$$

$$G_z = G_s$$

By determining an estimate of the overall peripheral nerve stimulation with both polarities, i.e., with inverted and non-inverted logical axis, it can be determined which polarity leads to a higher PNS and which leads to a lower PNS. Overall peripheral nerve stimulation may in particular be understood such that the peripheral nerve stimulation is considered by taking into account the contribution of all physical axes. In the following, when the estimate of the PNS is mentioned, usually the overall PNS or the peak of the overall PNS is meant, unless otherwise noted or implied. Depending on the geometrical setup, an inversion of the polarity of one logical gradient axis may lead to a smaller contribution of a particular physical gradient axis while increasing the contribution of another axis. If this particular physical gradient axis that now has a smaller contribution to the scan has a very high general contribution to PNS, the overall PNS and/or, in particular, the peak PNS may advantageously be significantly reduced by selecting the polarity that causes the lower PNS. Hence, a physical gradient activity may be moved to a physical gradient axis that is less stimulating in the sense of the PNS. On the other hand, the inversion of the polarity has usually no negative impact on the scan and the scan quality. Thus, the PNS may be reduced without adversely affecting scan quality or gradient performance. Further, advantageously, the method may be easily adaptable to different MRI sequences.

According to an embodiment, the estimate of the peripheral nerve stimulation (PNS) is determined based on durations, waveforms, and number of applied gradient pulses required for the whole or part of the planned magnetic resonance imaging scan. The waveforms may be implicitly derived by simulating the protocol, in particular without having to explicitly determine or input the waveforms. For the estimate, the gradient signal or a simulation of the gradient signal may be differentiated, rectified, optionally processed with lowpass filters, and summed, in particular by a weighted summation, in order to determine the PNS. For example, steeper flanks of the gradient pulses may lead to an increased PNS. The PNS may be calculated only for part of the protocol, in particular for a part that includes particularly short gradient pulse trains. Short gradient pulse trains may lead to increased occurrence of PNS. For example, the SAFE (Stimulation Approximation by Filtering and Evaluation) model, described by Franz X. Hebrank and Matthias Gebhardt in "SAFE-Model—A New Method for Predicting Peripheral Nerve Stimulations in MRI", Proceedings of the 8th Annual Meeting of ISMRM; Denver. 2000; 2007, may be used to estimate the PNS. Advantageously, the SAFE model may provide good reliability for estimating PNS without needing explicit knowledge of gradient waveforms and rise times. Furthermore, the SAFE model may handle both trapezoidal and sinusoidal gradient pulses well.

According to an embodiment, the acts (b)-(d) of determining the estimate of the peripheral nerve stimulation with both gradient polarities and selecting a gradient polarity are carried out for at least two, optionally all three, of the three logical gradient axes. Hence, the PNS may advantageously be minimized with respect to several logical gradient axes. For example, the acts (b)-(d), may be repeated with all possible combinations of gradient polarity, which results in 8 different combinations (two possible polarities on each of three axes). Alternatively, only the gradient polarity of two axes is inverted, resulting in 4 different combinations.

According to an embodiment, the estimate of the peripheral nerve stimulation is determined based on multiple simulations of the planned magnetic resonance imaging scan, one for each permutation of polarity of at least two logical gradient axes, preferably for all the logical gradient axes that are not parallel to any physical gradient axis. A set of gradient polarities is selected that has the lowest peripheral nerve stimulation according to the estimate. Advantageously, the overall contribution of multiple, preferably all, physical gradient axes that are not parallel to the logical gradient axes may thus be taken into account.

According to an embodiment, the estimate of the peripheral nerve stimulation is based on characteristic constants of the individual physical gradient axes, the characteristic constants being a measure for the individual physical gradient axes' contribution to the peripheral nerve stimulation. Hence, this embodiment may provide a model that takes into account the gradient design of the MRI system and the corresponding impact of the individual coils on the PNS. For example, the overall PNS due to all physical axes may be calculated by a weighted normalization using the characteristic constants. For example, the calculation of the overall PNS $S_{norm}$ may be as follows (Eq. 3):

$$S_{norm}(t)=\sqrt{\left(\frac{S_x(t)}{\mathrm{Slim}_x}\right)^2+\left(\frac{S_y(t)}{\mathrm{Slim}_y}\right)^2+\left(\frac{S_z(t)}{\mathrm{Slim}_z}\right)^2}$$

Where $S_{norm}(t)$ is a measure for the time-dependent PNS normalised to a given threshold and $S_{x,y,z}(t)$ are the rectified time-dependent derivatives, i.e., the absolute values of the derivatives, of the physical gradient signals of the physical gradient coils along the three physical gradient axes. For example, $S_{norm}(t)$ may be normalised such that a value greater than 1 indicates a PNS that is too high. $\mathrm{Slim}_{x,y,z}$ are the characteristic constants of the individual physical gradient axes. Hence, the overall PNS $S_{norm}(t)$ is weighted based on the characteristic constants. For example, on a state-of-the-art commercial system, the characteristic constant of one physical axis (e.g., $\mathrm{Slim}_x$ of the x-axis) may be about a factor of two higher compared to the characteristic constant of the other two physical axes (e.g., $\mathrm{Slim}_y$ of the y-axis and $\mathrm{Slim}_z$ of the z-axis). Therefore, in this example, the gradients of the y-axis and the z-axis contribute significantly more to the overall PNS than the gradient of the x-axis. The characteristic constants may, for example, be determined by tests on volunteers, such as explained by C. L. G. Ham et al. in "A. Peripheral Nerve Stimulation during MRI: Effects of High Gradient Amplitudes and Switching Rates", J. Magn. Reson. 1997; 7:933-937, and by defining corresponding threshold values based on the outcome of the tests. Advantageously, characteristic constants may provide an easy to implement solution to realize the estimation of the PNS depending on the scan protocol and the polarity of the at least one logical gradient axis.

According to an embodiment, at least the polarity of the logical gradient axis which has a substantial vector component in the direction of the physical gradient axis having the highest individual contribution to the peripheral nerve stimulation is inverted and estimated. The physical gradient axis having the highest individual contribution to the PNS may for example be determined by the characteristic constant described above. Advantageously, the reduction of PNS may be particularly high when applying this embodiment.

According to an embodiment, act (c) of the method is only carried out if the estimate of act (b) exceeds a predefined threshold, and wherein the polarity of act (b) is selected in act (d) if the estimate of act (b) does not exceed the predefined threshold. The method may include an additional act of checking whether the PNS estimated in act (b) exceeds the predefined threshold, wherein the additional is carried out before act (c). The predefined threshold may correspond to a PNS that is expected to be at the verge of being noticed by a subject. For example, a threshold corresponding to the thresholds determined by C. L. G. Ham et al. in "A. Peripheral Nerve Stimulation during MRI: Effects of High Gradient Amplitudes and Switching Rates", J Magn Reson. 1997; 7:933-937 may be used as predefined threshold. This embodiment may be advantageous in that it is checked whether the PNS is significant so that inverting the gradient polarity may potentially bring any benefit or whether the PNS is so low (or non-existent) that considering an inversion of the gradient polarity is not necessary and would therefore not bring any actual benefit. The method may include a further act of checking whether the inverted gradient polarity causes a PNS that is also below the predefined threshold. A notification warning may be sent to the user if both polarities exceed the predefined threshold. Hence the user may be warned that even when inverting the polarity, the PNS might be too high. Alternatively, the method may include a further act of checking whether both gradient polarities cause a PNS that is below a second predefined threshold. A notification warning may be sent to a user if the second predefined threshold is exceeded by both gradient polarities. The second predefined threshold may be higher than the first threshold. For example, the first threshold may be preferred not to be exceeded but may be still acceptable, whereas exceeding the second threshold may be not acceptable.

According to an embodiment, the magnetic resonance imaging is a gradient echo protocol or a turbo spin-echo protocol. For example, the gradient echo protocol may be an MP-RAGE protocol. Gradient echo protocol such as turbo spin-echo protocol may be characterized by particularly short gradient pulse trains. This may lead to an increased occurrence of peripheral nerve stimulation. Hence, the method may be particularly advantageous in the context of this embodiment.

According to an embodiment, the magnetic resonance imaging scan is an oblique scan, in particular a heart imaging scan. For example, the MRI scan may include a "BEAT" sequence by Siemens. Heart imaging may often include imaging planes and may thus be particularly well-suited to be used with the method.

According to an embodiment, the three logical gradient axes are rotated with respect to the three physical gradient axes around at least one of the physical gradient axes by at least 20°, preferably 30° to 60°, more preferably 40° to 50. A rotation closer to 45° may typically increase the effect of gradient polarity inversion on the PNS. Thus, the method may be more effective in this case. A rotation of essentially 45° may be particularly advantageous, since the effect of the inversion of logical gradient axes on the physical gradient axes may be easier to calculate, e.g., from Eq. 1 and Eq. 2 from above with θ=45° follows the relation (Eq.4):

$$G_x = -G_{y'}$$

$$G_y = -G_{x'}$$

Hence, the negative first physical gradient axis $-G_{x'}$ takes the role of the second physical gradient axis $G_y$ and the negative second physical gradient axis $-G_{y'}$ takes the role of the first gradient axis $G_x$. Accordingly, in this particular example, the influence of these two physical gradient axes on the PNS may be reversed. This may be particularly advantageous, when one of the two corresponding physical gradient axes has a significantly greater contribution to PNS, e.g., as defined by the characteristic constant such as $Slim_{x,y,z}$ in Eq. 3 above.

According to a further aspect, a computer program is provided. The computer program includes instructions which, when the program is executed on a magnetic resonance imaging system cause the magnetic resonance imaging system to carry out the acts of the method as described herein. All features and advantages of the method may be adapted to the computer program and vice versa.

According to a further aspect, a magnetic resonance imaging system is provided. The magnetic resonance imaging system has three physical gradient axes and is configured to perform a magnetic resonance imaging scan on a subject in which a field-of-view of the scan is positioned obliquely through the subject such that at least two of the logical gradient axes of the scan are not parallel to any of the physical gradient axes. The magnetic resonance imaging system is configured to:

- determine an estimate of the peripheral nerve stimulation for the magnetic resonance imaging scan to be performed,
- invert the gradient polarity of at least one logical gradient axis of the scan that is not parallel to any of the physical gradient axes and determine an estimate of the peripheral nerve stimulation for the planned magnetic resonance imaging scan with the inverted polarity,
- select the gradient polarity of the at least one logical gradient axis which has the lowest peripheral nerve stimulation, and
- perform the planned magnetic resonance imaging scan on the subject with the selected gradient polarity.

All features and advantages of the method and the computer program may be adapted to the magnetic resonance imaging system and vice versa. In particular, according to an embodiment, the magnetic resonance imaging system may be configured to carry out the method acts as described herein when carrying out the oblique magnetic resonance scan. The system may include a processing unit, in particular to carry out the simulation acts such as determining, inverting, and/or the selecting act. The processing unit may, for example, be or include a computer or part of a computer. The computer may be a PC, a server, and/or a control unit of the system. The computer may also be a mobile device, such as a laptop, tablet computer or mobile phone.

BRIEF DESCRIPTION OF THE DRAWINGS

The accompanying drawings illustrate various exemplary embodiments and methods of various aspects of the invention.

Similar elements are designated with the same reference signs in the drawings.

DETAILED DESCRIPTION OF THE DRAWINGS

Figure 1:
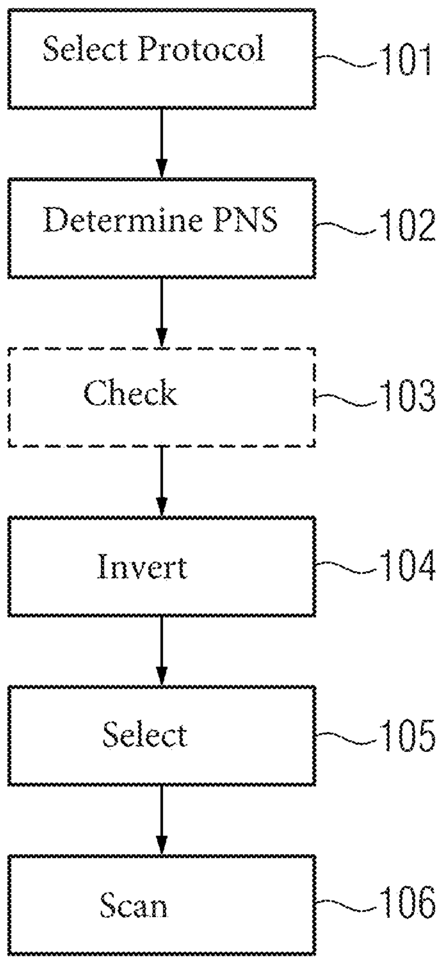
FIG. 1 shows a flow diagram of a method for reducing peripheral nerve stimulation in a subject during a magnetic resonance imaging scan according to an embodiment.
Figure 2:
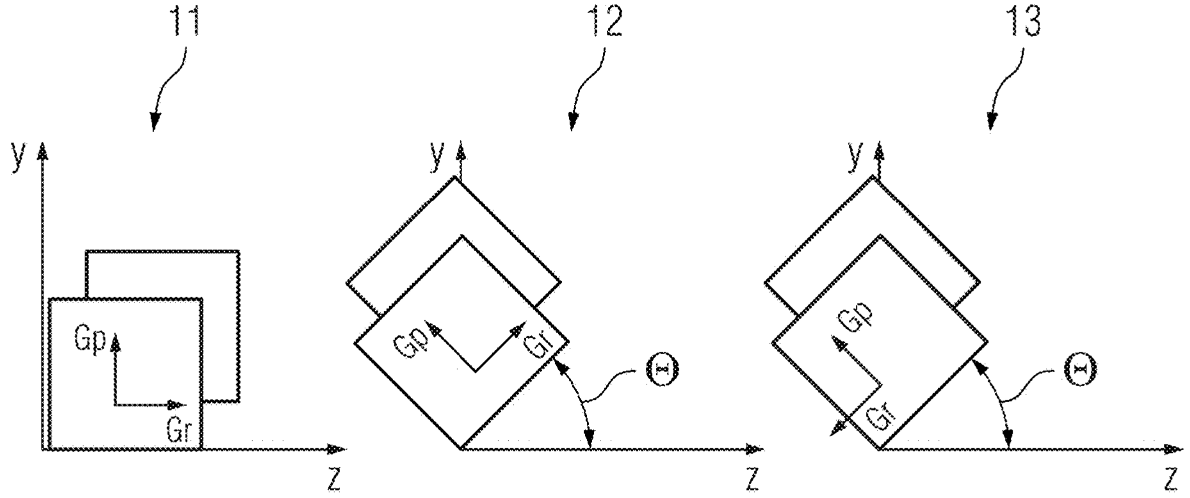
FIG. 2 shows an example representation of a non-rotated imaging plane and of oblique imaging planes with non-inverted read-out gradient and inverted read-out gradient, respectively.

FIG. 1 shows a flow diagram of a method for reducing peripheral nerve stimulation in a subject 5 during a magnetic resonance imaging scan according to an embodiment. For example, the magnetic resonance imaging scan may be a gradient echo protocol or a turbo spin echo protocol. In a first act 101, a magnetic resonance imaging scan is planned by selecting an imaging protocol and positioning a field-of-view of the scan obliquely through the subject 5. Obliquely means, that the logical gradient axes are rotated at least once with respect to the physical gradient axes. The logical gradient axes are typically read-out axis, the slice-select axis, and the phase-encode axis/axes. Hence, when the rotation is about one of the physical gradient axes, at least two of the logical gradient axes of the scan are not parallel to any of the physical gradient axes. For example, the logical gradient axes may be rotated by 45°. In a further act 102, an estimate of the peripheral nerve stimulation for the planned magnetic resonance imaging scan is determined. Preferably, the peripheral nerve stimulation may be determined based on at least one duration, at least one waveform and a number of applied gradient pulses that are required for the whole or part of the planned magnetic resonance imaging scan. These parameters may be regarded automatically in the context of a simulation of the peripheral nerve stimulation. Additionally and/or alternatively, the estimate of the peripheral nerve stimulation may be based on characteristic constants of the individual physical gradient axes that are a measure for the individual physical gradient axes' contribution to the peripheral nerve stimulation. At this point, there may be an optional act 103 of checking whether the peripheral nerve stimulation that has just been estimated exceeds a pre-defined threshold. It may thus optionally be provided to only carry out the following act 104 when the estimate of this optional act 103 exceeds a pre-defined threshold. Without this optional act 103, or whenever the estimate exceeds the pre-defined threshold, a further act 104 is carried out. In this further act 104, the gradient polarity of at least one logical gradient axis of the scan that is not parallel to any of the physical gradient axes is inverted, and the peripheral nerve stimulation for the planned magnetic resonance imaging scan with the inverted polarity is estimated. In a further act 105, the gradient polarity of the at least one logical gradient axis which has the lowest peripheral nerve stimulation is selected. Optionally, if the optional act 103 has been carried out and the peripheral nerve stimulation estimated in act 102 does not exceed the pre-defined threshold the polarity used in act 102 may be selected in this act 105. The acts 102 to 105 may optionally be carried out for at least two, optionally all three, of the three logical gradient axes. Hence the estimate of the peripheral nerve stimulation may be carried out with regard to several of the logical gradient axes. This may be done individually for each logical gradient axis or, alternatively, the estimate of the peripheral nerve stimulation may be determined based on multiple simulations of the planned magnetic resonance imaging scan, such that one simulation is carried out for each permutation of polarity the logical gradient axes, preferably for all the logical gradient axes that are not parallel to any physical gradient axis. A set of gradient polarities may then be selected that has the lowest peripheral nerve stimulation according to the estimate. In a further act 106, the planned magnetic resonance imaging scan is performed on the subject 5 with the selected gradient polarity FIG. 2 shows a representation of a non-rotated imaging plane 11 and of oblique imaging planes 12, 13 with non-inverted read-out gradient $G_r$ 12 and inverted read-out gradient $G_r$ 13. The gradient directions may be defined with respect to a subject coordinate system. Therein, y may be the anterior-posterior axis (vertical) and z may be the axis parallel to the magnet axis. For the non-rotated imaging plane, the logical gradients ($G_r$, $G_p$) are parallel to the physical gradients ($G_z$, $G_y$), such that in this example (Eq. 5):

$$G_z = G_r$$

$$G_y = G_p$$

In the centre 12 and on the right 13, a rotation of the imaging plane about the physical x-axes by the angle θ is shown. In the centre, the logical read-out gradient $G_r$ is not inverted. Hence the relation between the physical gradients ($G_z$, $G_y$) and the logical gradients ($G_r$, $G_p$) is (Eq. 6):

$$G_z = G_r\cos\theta - G_p\sin\theta$$

$$G_y = G_r\sin\theta + G_p\cos\theta$$

On the right 13, the read-out gradient $G_r$, is inverted such that relation between the physical gradients ($G_{z'}$, $G_{y'}$) and the logical gradients ($G_r$, $G_p$) is now (Eq. 7):

$$G_{z'} = -G_r\cos\theta - G_p\sin\theta$$

$$G_{y'} = -G_r\sin\theta + G_p\cos\theta$$

Inverting the logical gradient axis can be particularly advantageous when one of the physical gradients (here: $G_{z'}$, $G_{y'}$) that are related to this logical gradient (here: $G_r$) has a high, in particular the highest, individual contribution to the peripheral nerve stimulation (PNS) and when the contribution of this high-PNS physical gradients to the logical gradients can be reduced by the inversion.

The above relation can be simplified, if the angle of rotation θ is 45°, since cos45°=sin45°, such that it follows from Eq. 6 and Eq. 7 (Eq. 8):

$$G_z = -G_{y'}$$

$$G_y = -G_{z'}$$

Figure 3:
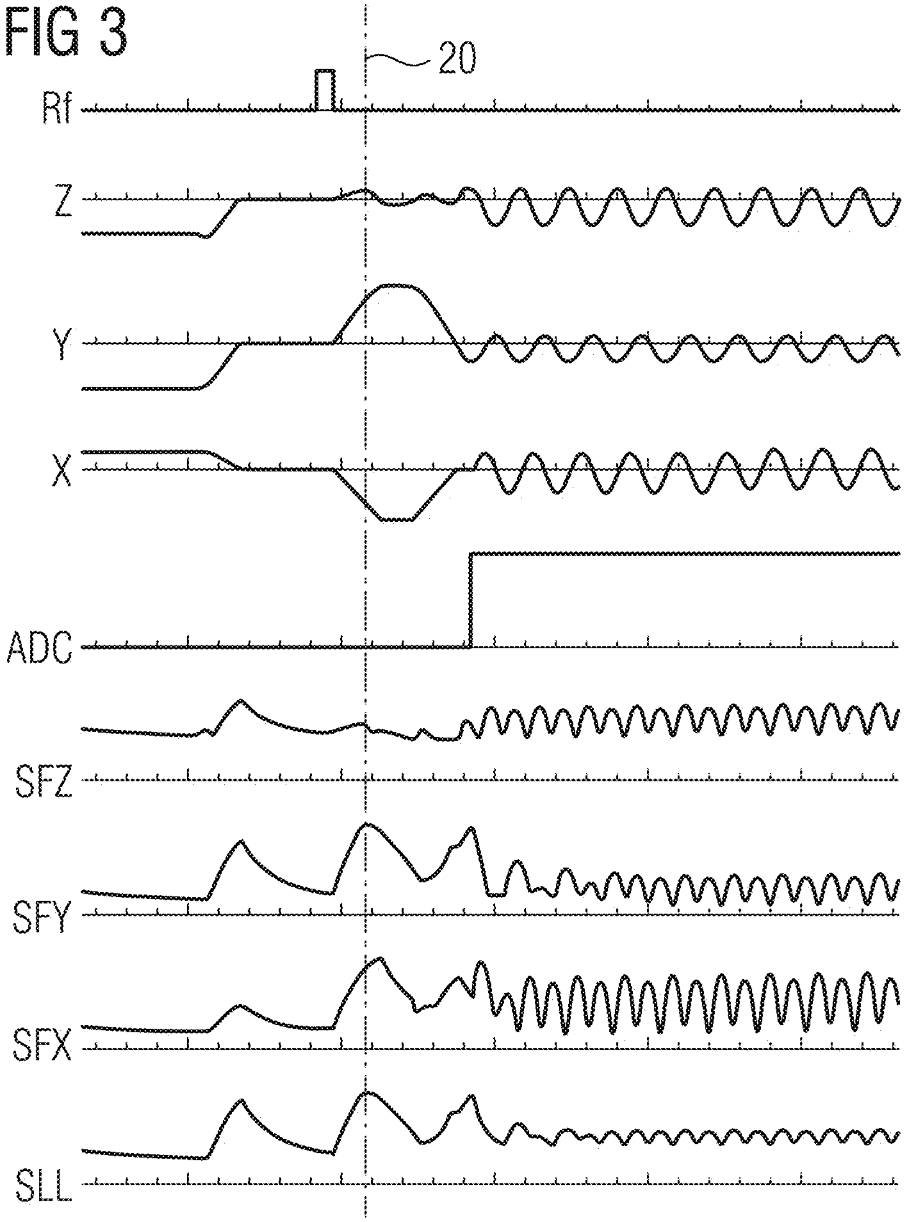
FIG. 3 shows part of an example simulated imaging sequence with an in-plane rotation of 45° and non-inverted read-out axis.
Figure 4:
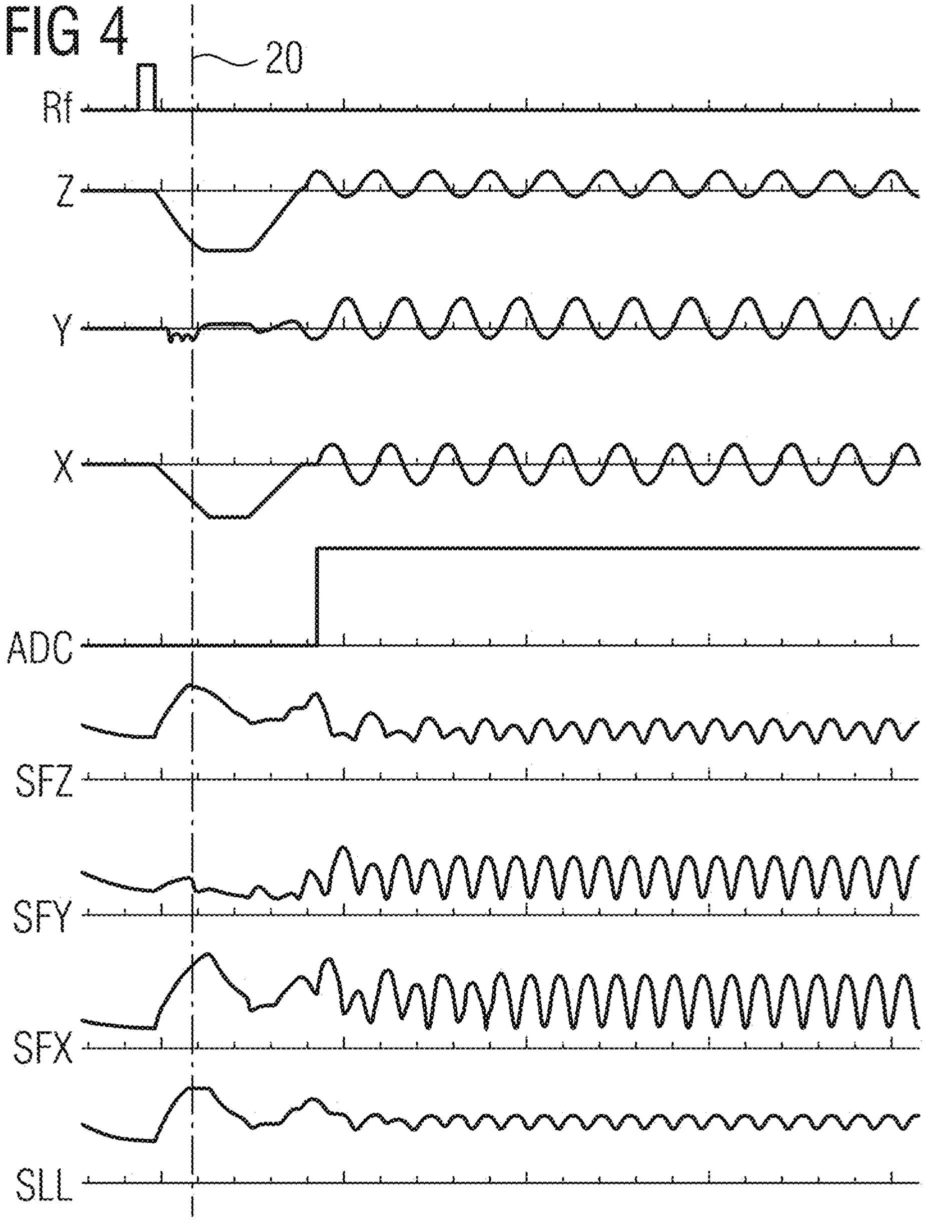
FIG. 4 shows part of an example simulated imaging sequence with an in-plane rotation of 45° and inverted read-out axis.

This particular case of an in-plane rotation of θ=45° is treated in the following example of oblique imaging shown in FIGS. 3 and 4. FIGS. 3 and 4 each show corresponding parts of a simulated imaging sequence with in-plane rotation of 45°, wherein in FIG. 4, the logical read-out axis has been inverted with respect to the imaging sequence shown in FIG. 3. The data are taken from a simulation of a sagittal WAVE MPRAGE imaging sequence. Both sequences show the RF signal, the gradient lobes of the physical gradient axes (Z, Y, X), and the corresponding PNS signal determined by the derivative of the physical gradient axes' signal (SFZ, SFY, SFX) as well as the overall PNS (SLL). The overall PNS (SLL) is determined by a weighted summation of the PNS of the individual axes (SFZ, SFY, SFX). The weighting is according to the individual contribution of gradient lobes of the individual physical gradient axis to the PNS that depends on the setup and construction (such as coil winding) of the imaging system 1. As defined by Eq.5, Eq. 6 and Eq. 7, the logical read-out $G_r$ is a combination of the physical gradients $G_z$ and $G_y$. In Order to determine the PNS, the maximal value of the SLL is taken, the position of which in the sequence is shown by a vertical line in both FIG. 3 and FIG. 4. At this position, the values of the physical gradients (denoted by X, Y, Z) are in FIG. 3:

$$G_z = 3.25$$

$$G_y = 24.28$$

$$G_x = -15.36$$

From these physical gradient values follows a maximum total stimulation PNS of 0.86 that can be taken from the line SLL (absolute values have been read-out electronically). In FIG. 4, the values of the physical gradients are as follows:

$$G_{z'} = -24.28$$

$$G_{y'} = -3.25$$

$$G_{x'} = -15.36$$

Hence, in FIG. 4, with inverted read-out gradient, the values of the logical gradients in z-and y-direction have been exchanged and multiplied by −1 according to Eq. 8. $G_{x'}$ on the other hand, has not changed. From this inversion of the read-out axis, follows a maximum total stimulation PNS of 0.69 (SLL). Hence, by inverting the read-out axis, the PNS has been reduced by more than 20% in this example.

Figure 5:
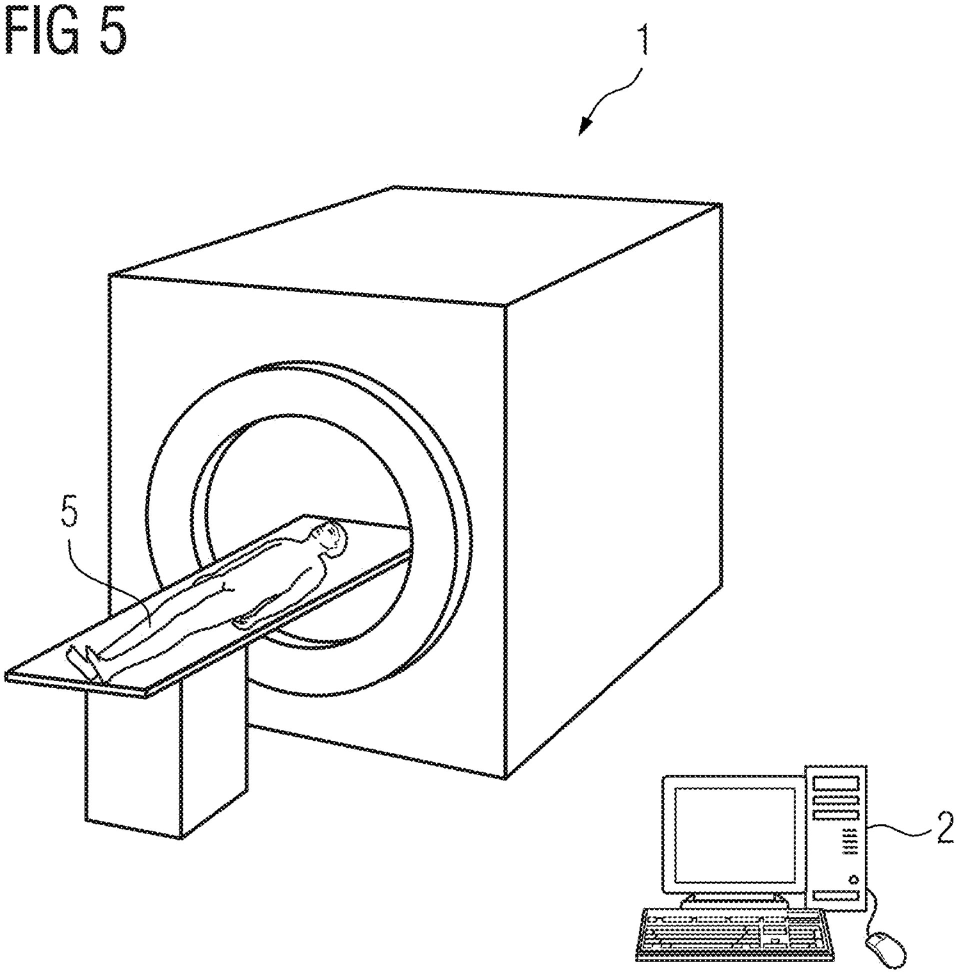
FIG. 5 shows a magnetic resonance imaging system according to an embodiment.

FIG. 5 shows a magnetic resonance imaging system 1 according to an embodiment. The system 1 has three physical gradient axes and is configured to perform a magnetic resonance imaging scan on a subject 5 in which a field-of-view of the scan is positioned obliquely through the subject 5 such that at least two of the logical gradient axes of the scan are not parallel to any of the physical gradient axes. The system 1 is in particular configured to carry out the method as described herein using a processing unit (processor or computer) 2.

Although the invention has been illustrated and described in greater detail with the preferred exemplary embodiment, the invention is not restricted to the examples disclosed, and other variants can be derived therefrom by a person skilled in the art, without going beyond the scope of the invention. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

The invention claimed is:

1. A method for reducing peripheral nerve stimulation in a subject during a magnetic resonance imaging scan of the subject using a magnetic resonance system having three physical gradient axes, the method comprising:

a) planning the magnetic resonance imaging scan by selecting an imaging protocol and positioning a field-of-view of the scan obliquely through the subject, such that at least two logical gradient axes of the scan are not parallel to any of the physical gradient axes;

(b) determining an estimate of an overall peripheral nerve stimulation for the planned magnetic resonance imaging scan based on:

at least one duration, at least one waveform, and a number of applied gradient pulses required for all or part of the planned magnetic resonance imaging scan;

characteristic constants of the three physical gradient axes that are measures for contributions of the three physical gradient axes to the overall peripheral nerve stimulation, respectively; or the at least one duration, the at least one waveform, the number of applied gradient pulses, and the characteristic constants;

(c) inverting a gradient polarity of at least one logical gradient axis of the scan that is not parallel to any of the physical gradient axes and determining an estimate of the overall peripheral nerve stimulation for the planned magnetic resonance imaging scan with the inverted polarity;

(d) selecting the gradient polarity of the at least one logical gradient axis which has a lowest overall peripheral nerve stimulation; and (e) performing the planned magnetic resonance imaging scan on the subject with the selected gradient polarity.

2. The method according to claim 1, wherein act (d) comprises selecting the gradient polarity that has a lowest maximum of the overall peripheral nerve stimulation across the imaging protocol.

3. The method according to claim 1, wherein the estimate of the overall peripheral nerve stimulation is determined based on durations of the at least one duration, waveforms of the at least one waveform, and the number of applied gradient pulses required for all or part of the planned magnetic resonance imaging scan.

4. The method according to claim 1, wherein the acts (b)-(d) of determining the estimate of the overall peripheral nerve stimulation with both gradient polarities and selecting a gradient polarity are carried out for two or more of three logical gradient axes.

5. The method according to claim 1, wherein the estimate of the overall peripheral nerve stimulation is determined based on multiple simulations of the planned magnetic resonance imaging scan, one for each permutation of polarity of at least two logical gradient axes, wherein a set of gradient polarities is selected that has the lowest overall peripheral nerve stimulation according to the estimate.

6. The method according to claim 5, wherein the peripheral nerve stimulation is determined based on multiple simulations of the planned magnetic resonance imaging scan, one for each permutation of polarity of all the logical gradient axes that are not parallel to any physical gradient axis.

7. The method according to claim 1, wherein the estimate of the overall peripheral nerve stimulation is based on characteristic constants of the physical gradient axes, the characteristic constants being a measure for the physical gradient axes' contribution to the peripheral nerve stimulation.

8. The method according to claim 7, wherein at least the polarity of the logical gradient axis which has a vector component in a direction of the physical gradient axis having the highest individual contribution to the peripheral nerve stimulation is inverted and estimated.

9. The method according to claim 1, wherein the magnetic resonance imaging is a gradient echo protocol or a turbo spin-echo protocol.

10. The method according to claim 1, wherein the magnetic resonance imaging scan is an oblique scan.

11. The method according to claim 10, wherein the oblique scan is a heart imaging scan.

12. The method according to claim 1, wherein the at least one logical axis comprises a read-out axis, a slice-select axis and/or a phase-encode axis or axes.

13. The method according to claim 1:

wherein the at least one logical axis comprises a slice-select axis; and wherein the polarity of a frequency of RF pulses is selected according to the selected polarity of the slice-select axis.

14. The method according to claim 1, wherein three logical gradient axes are rotated with respect to the three physical gradient axes around at least one of the physical gradient axes by at least 20°.

15. The method according to claim 14, wherein the three logical gradient axes are rotated with respect to the three physical gradient axes around at least one of the physical gradient axes by 40° to 50°.

16. A magnetic resonance imaging system having three physical gradient axes and being configured to perform a magnetic resonance imaging scan on a subject in which a field-of-view of the scan is positioned obliquely through the subject such that at least two logical gradient axes of the scan are not parallel to any of the physical gradient axes, wherein the magnetic resonance imaging system is configured to:

determine an estimate of an overall peripheral nerve stimulation for the magnetic resonance imaging scan to be performed based on:

at least one duration, at least one waveform, and a number of applied gradient pulses required for all or part of the magnetic resonance imaging scan to be performed;

characteristic constants of the three physical gradient axes that are measures for contributions of the three physical gradient axes to the overall peripheral nerve stimulation, respectively; or the at least one duration, the at least one waveform, the number of applied gradient pulses, and the characteristic constants, invert a gradient polarity of at least one of the logical gradient axes of the scan that is not parallel to any of the physical gradient axes and determine an estimate of the overall peripheral nerve stimulation for the magnetic resonance imaging scan with the inverted polarity, select the gradient polarity of the at least one logical gradient axis which has the lowest overall peripheral nerve stimulation, and perform the magnetic resonance imaging scan on the subject with the selected gradient polarity.

17. The magnetic resonance imaging system according to claim 16, wherein the magnetic resonance imaging system is configured to estimate the peripheral nerve stimulation based on durations of the at least one duration, waveforms of the at least one waveform, and the number of applied gradient pulses for all or part of the magnetic resonance imaging scan.

18. The magnetic resonance imaging system according to claim 16, wherein the magnetic resonance imaging scan is a gradient echo protocol scan or a turbo spin-echo protocol scan.

19. The magnetic resonance imaging system according to claim 16, wherein the magnetic resonance imaging system is configured to only carry out the invert of the gradient polarity of the at least one logical gradient axis and the determination of the estimate of the overall peripheral nerve stimulation for the magnetic resonance imaging scan with the inverted polarity when the estimate of the overall peripheral nerve stimulation for the magnetic resonance imaging scan to be performed exceeds a pre-defined threshold, and wherein the polarity of the determined estimate of the overall peripheral nerve stimulation for the planned magnetic resonance imaging scan is selected in the selection when the estimate of the overall peripheral nerve stimulation for the magnetic resonance imaging scan to be performed does not exceed the pre-defined threshold.

* * * * *